United States Patent [19]

Ovil et al.

[11] Patent Number: 4,702,250
[45] Date of Patent: Oct. 27, 1987

[54] SURGICAL IMPLEMENT PARTICULARLY USEFUL FOR SUTURING PROSTHETIC VALVES

[75] Inventors: Yoel Ovil, Ramat Hasharon; Morris Levy, Tel-Aviv, both of Israel

[73] Assignee: Galil Advanced Technologies Ltd., Ramat Gan, Israel

[21] Appl. No.: 821,988

[22] Filed: Jan. 23, 1986

Related U.S. Application Data

[63] Continuation-in-part of Ser. No. 644,950, Aug. 28, 1984, abandoned.

[30] Foreign Application Priority Data

Sep. 2, 1983 [IL] Israel ..................................... 69635
Feb. 27, 1985 [IL] Israel ..................................... 74460

[51] Int. Cl.[4] ..................... A61B 17/04; A61B 17/00
[52] U.S. Cl. ............................ 128/334 R; 128/303 R
[58] Field of Search ............... 623/1; 128/334 R, 335, 128/303 R, 340, 335.5; 604/227

[56] References Cited

U.S. PATENT DOCUMENTS

2,915,064 12/1959 Everett et al. ...................... 604/227
3,409,013 11/1968 Berry .............................. 128/303 R
4,185,636 1/1980 Gabbay et al. ................. 128/334 R

Primary Examiner—Richard C. Pinkham
Assistant Examiner—Gary Jackson
Attorney, Agent, or Firm—Benjamin J. Barish

[57] ABSTRACT

A surgical instrument to aid in suturing a prosthetic valve into a heart annulus, comprises: a manually grippable handle, a holder carried at one end of the handle for releasably holding a prosthetic valve to be pre-loaded thereon, a first ring fixed to the handle and securing thereto one end of a plurality of sutures to be pre-loaded onto the handle with each suture carrying a needle at its opposite end passing through the prosthetic valve when pre-loaded on the handle; and a second ring fixed to the handle for releasably retaining the plurality of sutures each pre-loaded in folded condition on the handle and extending longitudinally thereof. The two rings are located on the handle such that each suture has a length between the prosthetic valve and the needle-carrying end of the suture which is at least twice the length of the suture between the secured one end and the prosthetic valve.

18 Claims, 17 Drawing Figures

SURGICAL IMPLEMENT PARTICULARLY USEFUL FOR SUTURING PROSTHETIC VALVES

RELATED APPLICATION

The present application is a continuation-in-part of our co-pending application Ser. No. 06/644,950, filed Aug. 28, 1984 now abandoned.

BACKGROUND OF THE INVENTION

The present invention relates to surgical implements for use in applying sutures. The invention is particularly useful in surgical operations for the attachment of prosthetic valves, and it is therefore described below with respect to this application, but it will be appreciated that the invention could advantageously be used in other applications as well.

The surgical replacement of devective heart valves, both the aortic valve and the mitral valve, has become a widely-practiced technique. In such a surgical operation, the defective natural valve is surgically removed, and a prosthetic valve is applied by a number of sutures, varying from 12-20 depending upon the size of the annulus remaining after removing the defective natural valve. In this surgical operation, the prosthetic valve to replace the natural one is usually held in a holder while each of the sutures is individually applied, first to the annulus and then to the valve on the holder; and after all the sutures have been applied to both, the valve is moved into the annulus and is fixed in place by knotting the sutures and trimming their ends.

The existing procedures using valve holders and other implements presently available require a considerable period of time because of the large number of sutures which must be applied first to the annulus, and then to the valve, before the valve is moved into position within the annulus. Moreover, such a procedure requires a large number of attendants, particularly because of the many different tissues and different tissue points which must be maintained retracted during the surgical operation. Another very serious difficulty involved in the existing procedure is the danger of entanglement of the sutures to be applied to the body annulus and to the valve while the valve is held externally of the body, before the valve can be moved into the body annulus. All these drawbacks in the existing procedures using the presently available implements increase the time required for the surgical operation, the danger to the patient, the fatigue of the surgeon, and the number of attendants required for assistance.

It has been previously proposed to use various types of surgical instruments including holders for prosthetic devices and sutures, as illustrated for example in U.S. Pat. Nos. 4,185,636 and 3,409,013, and Russian Pat. No. 207,339. However, insofar as we are aware, such instruments have not been found satisfactory and have not come into widespread use.

An object of the present invention is to provide a suturing implement which is particularly useful in surgical operations for the attachment of prosthetic valves and which, when so used, provide a number of advantages in the respects discussed above.

BRIEF SUMMARY OF THE INVENTION

According to one aspect of the present invention, there is provided a surgical instrument to aid in suturing a prosthetic valve into a heart annulus, comprising: a manually grippable handle, a holder carried at one end of the handle for releasably holding a prosthetic valve to be pre-loaded thereon, a first ring fixed to the handle and securing thereto one end of a plurality of sutures to be pre-loaded onto the handle with each suture carrying a needle at its opposite end passing through the prosthetic valve when pre-loaded on the handle; and a second ring fixed to the handle and including a plurality of circumferentially-spaced projections each engageable with an intermediate portion of a suture for releasably retaining the plurality of sutures each pre-loaded in folded condition on the handle and extending longitudinally thereof. The two rings are located on the handle such that each suture has a length between the prosthetic valve and the needle-carrying end of the suture which is at least twice the length of the suture between the secured one end and the prosthetic valve.

The invention can be embodied in a number of different constructions, several of which are described below for purposes of example.

Thus, in one described embodiment, both rings are secured to the handle at the opposite end from the valve holder such as to permit each suture to be initially folded to form three folds between its secured end and its needle end; in another described embodiment, the first ring is secured to the handle adjacent to the end carrying the holder, and the second ring is secured to the opposite end of the handle and includes a projection for each suture engageable by a mid-portion of the respective suture to permit it to be folded back to the first ring to provide, in the suture pre-loaded condition of the implement, at least two folds of the suture between the first and second rings.

According to another important feature, the handle includes a cross-bar at its outer end remote from the holder for gripping between the two fingers and thumb of the user when the implement is used to apply traction to the heart annulus.

The improved implement of the invention provides a number of important advantages when used for surgically attaching a prosthetic valve, as compared to existing techniques as well to those proposed in the above-identified prior art patents. These advantages will be more particularly described below .

BRIEF DESCRIPTION OF THE DRAWINGS

The invention is herein described, by way of example only, with reference to the accompanying drawings, wherein.

DESCRIPTION OF PREFERRED EMBODIMENTS

The Embodiment of FIGS. 1–8

Figures 1, 2, 3:
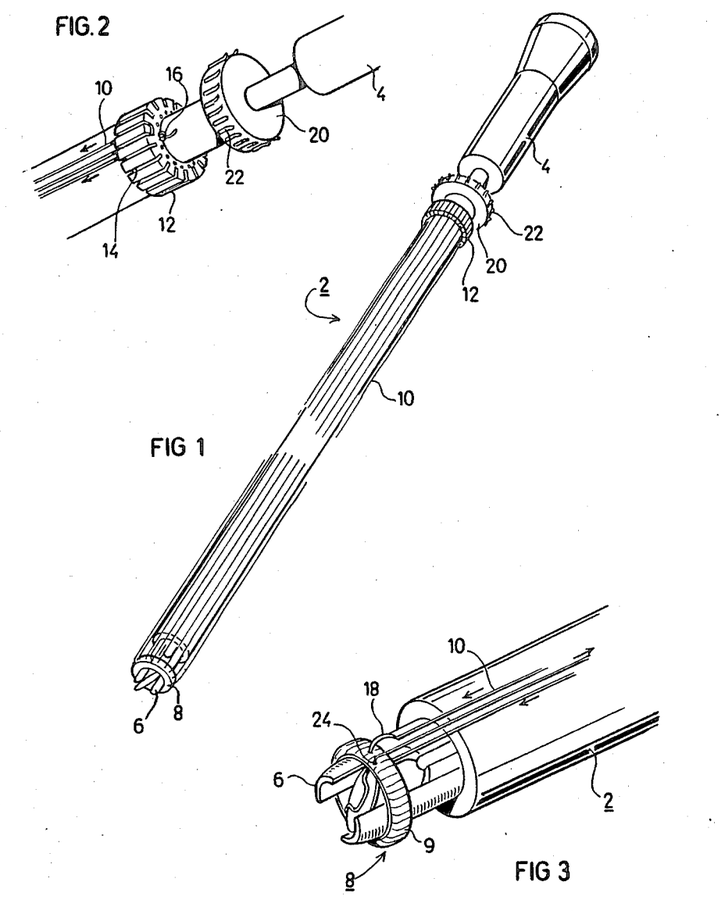
FIG. 1 is a three-dimensional view illustrating one form of suturing implement constructed in accordance with the invention for use in the surgical replacement of a heart valve.
FIG. 2 is an enlarged fragmentary view of the upper end of the implement of FIG. 1, particularly showing the manner of securing the sutures adjacent to its handle.
FIG. 3 is an enlarged fragmentary view illustrating the lower end of the implement of FIG. 1, particularly showing the free ends of the sutures and the prosthetic valve held at that end.

With reference to FIGS. 1–3, there is illustrated a suturing implement, generally designated 2, including a manually-grippable handle 4 at one end, and a valve holder 6 at the opposite end for releasably holding a prosthetic valve 8. The latter valve may be any one of the commercially available aortic or mitral valves, e.g. of the pivotable disc type, which valves include a peripheral mounting ring 9 through which the sutures are passed for suturing the prosthetic valve in place.

Implement 2 further includes a plurality of sutures 10 secured at one of their ends circumferentially around handle 4. For this purpose, the implement includes a ring 12 fixed at its upper end, adjacent to handle 4. Ring 12 is formed with a plurality of axially-extending circumferentially-spaced slots 14 for securing the ends of the sutures 10. This may be done by merely forming that end of the suture with a knot 16, and then passing the suture through its respective slot 14. The free end of each suture 10 carries a suture needle 18.

A second ring 20 is fixed to handle 4 and carries a plurality of circumferentially-spaced projections in the form of retainer clips 22 each engageable with an immediate portion of a suture for releasably retaining the plurality of sutures 10 pre-loaded in folded condition on the handle to extend longitudinally thereof. Ring 20 is located such that each suture has a length between the prosthetic valve and the needle-carrying end which is at least twice the length of the suture between the end secured to ring 12 and the prosthetic valve 8.

Figures 4, 5:
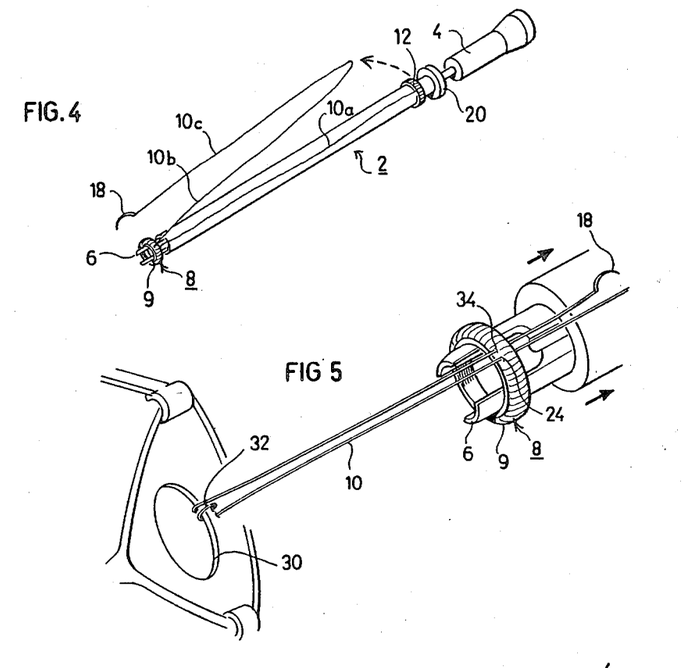
FIGS. 4–7 illustrate one preferred procedure of using the implement of FIGS. 1-3 for the surgical replacement of a heart valve.

In the embodiment of FIGS. 1–3, each of the sutures 10 is of a length approximately triple the distance between securing ring 12 at one end, and the valve holder 6 at the opposite end, so as to permit each suture to be initially folded to form three folds 10a, 10b, and 10c, as shown in FIG. 4. Each of the sutures 10 (there being 12–20, depending on the particular case) is initially loaded onto implement 2 by: passing its free end (carrying the suture needle 18) through the peripheral mounting ring 9 of the prosthetic valve 8 which is also initially loaded onto its holder 6; then folding the suture back to the opposite end of the implement adjacent to its handle 4, wherein the suture is releasably received in retainer clip 22 carried by a ring 20 fixed at that end of the holder; and then again folding the suture back to the prosthetic valve 8, whereat the suture needle is received in peripheral ring 9 of the valve.

Valve holder 6 is of the type which includes two fingers (FIG. 3) normally gripping the inner face of the valve mounting ring 9, the fingers being movable toward each other by the rotation of handle 4 to release the valve. Valve holders of this type are known (e.g. see the above-cited U.S. Pat. No. 3,409,013) and commercially available, and therefore further details of its construction are not included herein.

The implement illustrated in FIGS. 1–3 may be used in the following manner, reference being made to the sequence of steps illustrated in FIGS. 4–7.

Before the surgical operation, the holder 6 is first loaded with the prosthetic valve 8 to be used in the operation; and then all the sutures 10 to be used in suturing the valve in place are applied by knotting one of their ends and passing the suture through a slot 14 of securing ring 12. The free end (i.e., the end carrying the suture needle 18) is then passed through the peripheral ring 9 of the prosthetic valve 8 as shown at 24, FIG. 3; folded back and passed around its retainer clip 22 on the clip ring 20; and is then again folded back to bring its free end carrying the suture needle 18 towards valve 8, whereas the needle is received in the valve peripheral ring 9. This is all done before the surgical operation, preferably by the manufacturer supplying the implement preloaded with the prosthetic valve and the sutures.

During the surgical operation, the natural, defective valve is first surgically removed from the patient, and the annulus 30 (FIG. 5) is prepared for receiving the prosthetic valve 8. Implement 2, loaded with the sutures 10 and prosthetic valve 8, is held by an attendant over the subject's body with the prosthetic valve 8 facing, but spaced a distance from, the annulus 30 of the patient. Each suture 10 is then individually released from the holder and is applied to the annulus 30 of the subject in the following manner:

First, the suture needle 18 of the respective suture 10 is detached from ring 9 of the valve 8, and the suture is then unfolded by removing it from its retainer clip 20 at the upper end of the implement. The unfolded suture thus extends its full length, while the remaining sutures are retained folded and the valve 8 is retained in holder 6 (FIG. 4).

The suture needle 18 is then, in one operation: (a) passed through the heart annulus 30 (FIG. 5) to form an "over-and-over x", or two-looped, stitch 32; (b) passed through the valve ring 9 at 34, while the valve is still retained by holder 6 externally of the body; and (c) then received on its retainer clip 22 (FIG. 2) of retainer ring 20 at the handle-end of the implement.

It will be appreciated that, in the unfolded condition of the suture, one-third the length of the suture is available for bringing it from valve 8 to the heart annulus 30, and back to the valve, so that the distance between the valve and the heart annulus 30 is approximately one-sixth of the complete length of the suture. After the first suture has thus been applied, an attendant holding handle 4 of the implement, lighly pulls it away from the heart annulus 30, to thereby apply a traction force retracting the annulus and also placing the so-applied suture under tension. All the remaining sutures 10 are then applied in the same manner as described above, one after the other, while the attendant maintains the traction force on the implement, thereby maintaining the retraction of the annulus and the tension on each suture after it has been applied in its turn.

Figure 6:
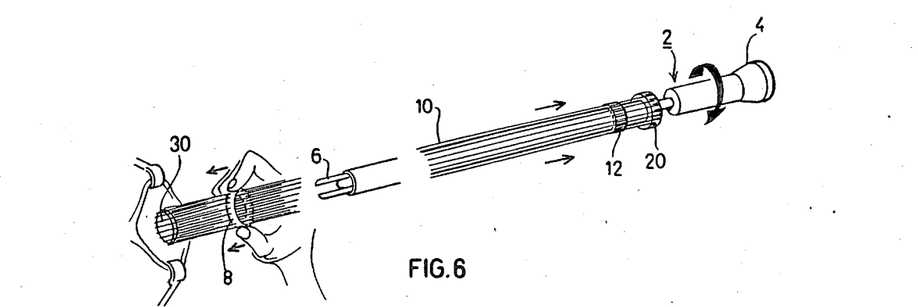
Figure 7:
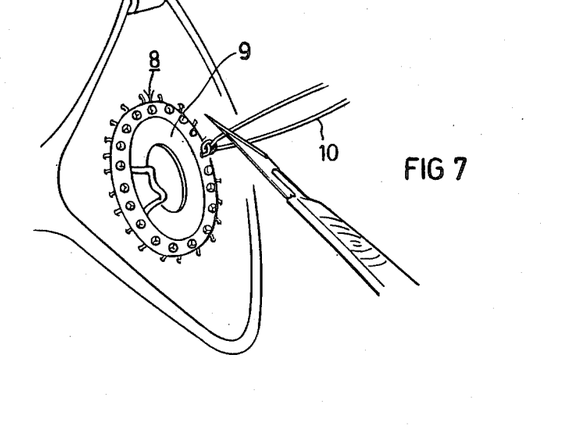

After all the sutures (12-20, according to the particular case) have been so applied, and while all the sutures are maintained under tension by the traction force applied to handle 4 by the attendant, handle 4 is rotated (FIG. 6) in order to move together the holder fingers 6 to release valve 8, whereupon the surgeon, while grasping the released valve between his thumb and index finger, slides the valve along the tensioned sutures 10 towards the patent and into the heart annulus 30. Each suture is then tied in place by first releasing its opposite ends from rings 12 and 20, and then forming one or more knots to securely hold the valve 8 within the annulus 30. After all the sutures have thus been secured, the free ends of all the sutures are trimmed (FIG. 7).

It will thus be seen that using the implement of FIGS. 1-3 in order to surgically attach a prosthetic valve, as described above with respect to FIGS. 4-7, provides a number of important advantages over the existing techniques. A major advantage is that since the implement, before the operation, is pre-loaded with the prosthetic valve and the sutures, with the sutures already passed once through the valve, the use of this pre-loaded implement very substantially reduces the time required for attaching the prosthetic valve to the heart annulus. In addition, the implement serves as a common retractor for exposing the complete annulus during the operation. Further, since the sutures, when in their unfolded condition, are all maintained under tension, there is substantially less danger of entanglement. Moreover, the tensioned sutures act as a guide for guiding the valve into proper position within the heart annulus during the step illustrated in FIG. 6, thereby better assuring correct placement of the valve in a minimum of time. All the foregoing advantages enable the operation to be performed in a substantially shorter period of time, and in a safer and more efficient manner, thereby substantially reducing the danger to the patient and also the fatigue to the surgeon.

Preferably, a number of the sutures 10 located at spaced points around the circumference (e.g., each fourth suture) may be visually distinguishable (e.g., by color-coding) from the remaining intermediate sutures. This enables such spaced sutures to be first applied in order to first secure the complete circumference of the valve to the heart annulus, whereupon the remaining intermediate sutures may be applied between these previously secured points. Such a technique may further increase the efficiency of the surgical procedure.

Figure 8:
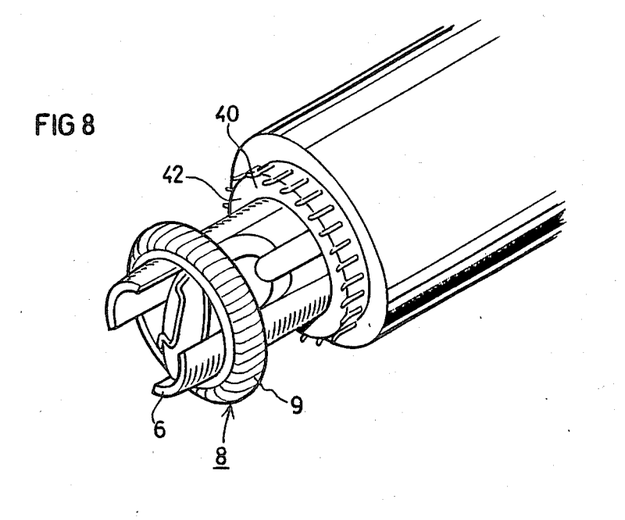
FIG. 8 illustrates a modification in the holder end of the implement of FIGS. 1-7.

In the above-described embodiment of the invention, the free ends of the sutures (i.e., the ends carrying the suture needles 18) are releasably retained, when the sutures are in their initial folded conditions, by passing their suturing needles through the valve mounting ring 9, as shown particularly in FIG. 3. In some cases it may be desirable to include a separate retaining ring at that end of the implement. This is shown in FIG. 8 wherein it will be seen that another retainer ring 40 is provided at the end of the implement adjacent to the valve holder 6. The latter ring includes a retainer clip 42 for releasably retaining the free end (carrying the suture needle 18) of each suture 10 in the folded condition of the sutures.

Figure 9:
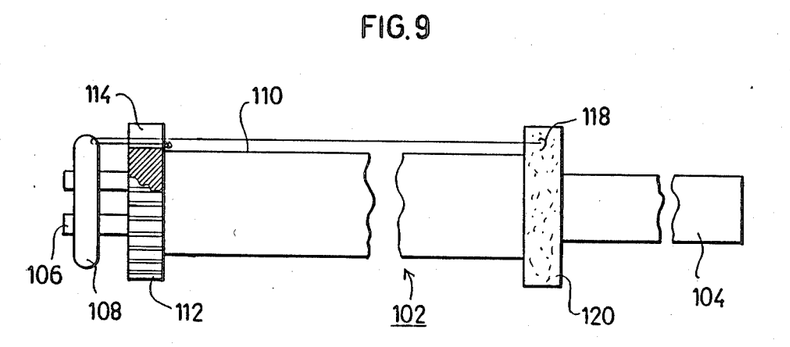
FIG. 9 illustrates another suturing implement constructed in accordance with the invention.
Figure 10:
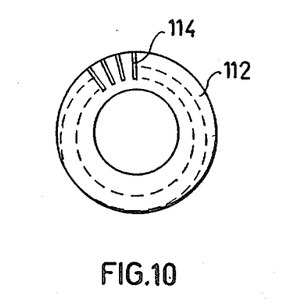
FIG. 10 is a fragmentary view illustrating the holder-end of the implement of FIG. 9.

The Embodiment of FIGS. 9 and 10

FIGS. 9 and 10 illustrate another suturing implement, generally designated 102, also including a handle 104 at one end, and a holder 106 at the opposite end for releasably retaining the prosthetic valve 108. In this case, the sutures 110 are secured to a securing ring 112 mounted at the inner end of the implement adjacent to the valve holder 106. Securing ring 112 is formed with a plurality of radially-extending slots 114 (FIG. 10) which are of substantial depth for accomodating the respective suture. Thus, the suture may be knotted at one end such that when received in a slot 114, its knot engages the upper face of ring 112. The suture is then passed through the rim of the valve 108 held by holder 106 in the same manner shown at 24 in FIG. 3, and is then folded back so as again to pass through its respective slot 114 to the upper (handle) end of the implement, wherein its suture needle 118 at its free end is removably retained in a ring 120 secured at that end.

Ring 120, as shown, may be a fabric ring enabling the suture needle 118 to penetrate it for releasably retaining this free end of the suture within it; alternatively, this ring could include a plurality of clip-type retainer elements for releasably retaining the free end of the suture.

This would be the initial, loaded condition of the implement 102, in which case it will be seen that each suture 110 need only be of a length slightly greater than the length of the implement between the two rings 112 and 120 to provide one run or fold of the suture in this initial condition of the implement.

During the operation, each suture 110 is released from its retainer ring 120, and its suture needle 118 is passed through the heart annulus and again through the rim of the valve 108, as described with respect to FIG. 5, except that here the free end of the suture is attached to the securing ring 112 at the lower end of the implement, rather than being brought back to the upper end of the implement. For thus securing the suture, it may be looped around the portion of ring 112 bordered by its respective slot 114 and the next adjacent slot of the precedingly applied suture (not of the subsequently-to-be-applied suture, since this would interfere with unfolding that suture in its turn). Thus, there would be one extra slot 114 adjacent to the slot for the first-to-be applied suture. Alternatively, securing ring 112 could be provided with two slots 114 for each suture, one slot for securing the knotted end of the suture and for accomodating the suture when folded back to the upper retainer ring 120, and a second adjacent slot for use with the first-mentioned slot for securing the free ends of the suture after it has been passed through the heart annulus and the second time through the valve. At that time, the suture needle 118 may be severed so as not to interfere with the application of the subsequent sutures.

All the sutures 110 are thus applied, one after the other, in the above-described manner while the implement 102 is continuously subjected to a traction force to expose the annulus and to tension the sutures, as described above with respect to the FIGS. 1-7 embodiment. Valve 108 is then released and is moved into the heart annulus, guided by the tensioned sutures, and the opposite ends of each suture are then severed and knotted, one after the other, after which the ends are trimmed, all as described above with reference to the FIGS. 1-7 embodiment.

If longer lengths of sutures are needed in their unfolded condition to permit the sutures to be applied to the heart annulus and back to the valve while the latter is retained within the holder 106, such longer suture lengths may be provided by folding the sutures back to the securing ring 112 and retaining their free ends, e.g. in slots formed in this ring. In such a case, the sutures would include two folds, rather than the single fold illustrated in the arrangement of FIG. 9.

The Embodiment of FIGS. 11–16

Figures 11, 11A:
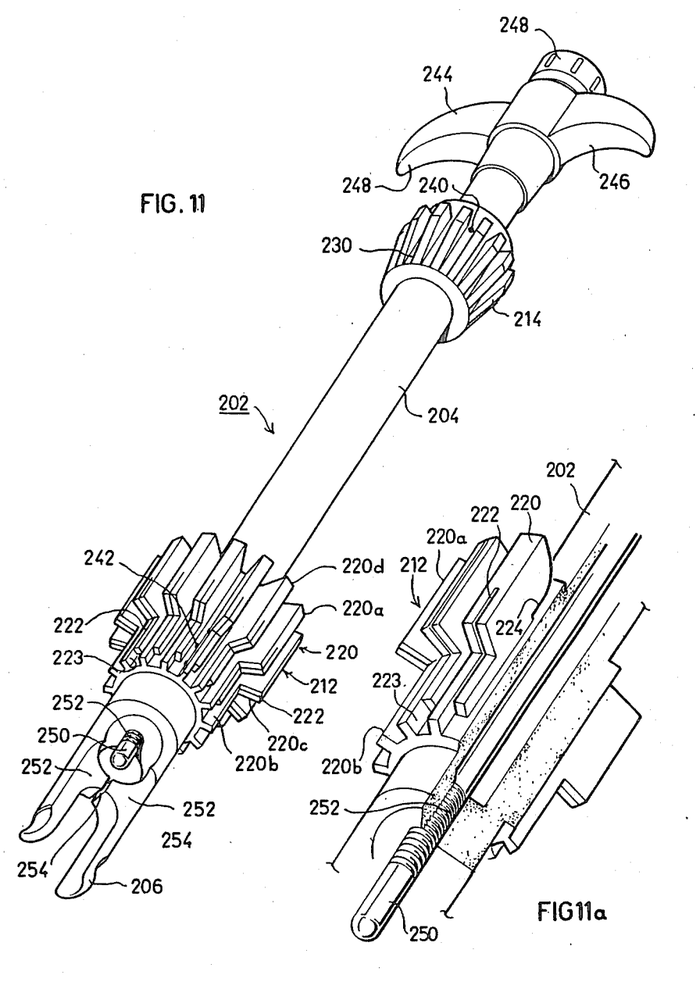
FIG. 11 is a three-dimensional view illustrating another form of surgical instrument constructed in accordance with the present invention.
FIG. 11a is a fragmentary view of a portion of FIG. 11 to show internal structure.
Figure 12:
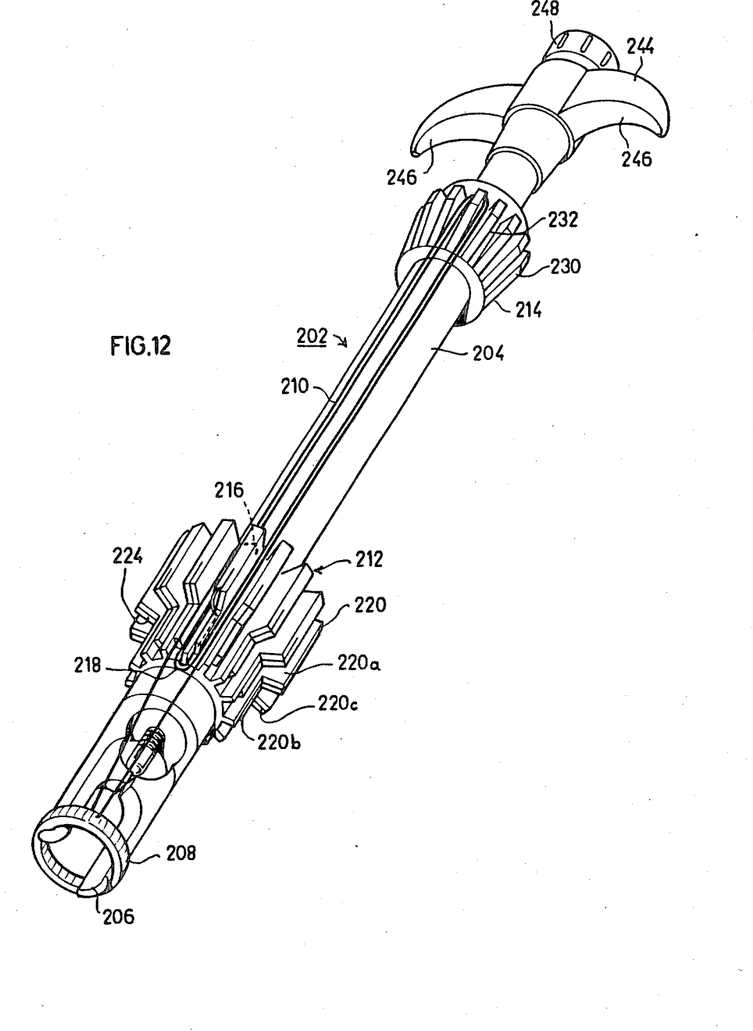
FIG. 12 illustrates the implement of FIG. 1 preloaded with a prosthetic valve and, (for purposes of clarity) with only one of the many (e.g. 12–20) sutures with which it would normally be pre-loaded.

This surgical implement, as illustrated in FIGS. 11 and 12, therein generally designated 202, includes a manually grippable handle 204 at one end, and a valve holder 206 at the opposite end for releasably holding a prosthetic valve 208 (FIG. 12) to be pre-loaded onto the implement. Also to be pre-loaded are a plurality of sutures 210, only one of which is illustrated in FIG. 12. For pre-loading sutures 210, implement 202 is provided with a first ring 212 fixed at the lower end of its handle 204 adjacent to the valve holder 206, and a second ring 214 fixed to the opposite, upper end of the handle.

Each of the sutures 210 is provided with a needle, shown at 216 and 218, respectively, at each of its opposite ends. Needle 216 at one end of the suture is used for fixing that end to the lower ring 212. The opposite end of the suture carrying needle 218 is first passed through the outer rim of prosthetic valve 208 held by holder 206, then folded back past ring 212 to the upper ring 214, then folded back to the lower ring 212, again folded back to the upper ring 214, and finally back to the lower ring 212, where its needle 218 is releasably held.

It will thus be seen that each suture, in the pre-loaded condition of the implement, is provided with a relatively small length between its point of attachment (needle 216) to the lower ring 212 and its passage through the prosthetic valve 208, the remaining length of each suture 212 including four folds equal to substantially four times the distance between rings 216 and 214. Needle 218 releasably held by ring 212 at the free end of the suture is used for passing the suture through the heart annulus. The substantial length of each suture between the prosthetic valve 208 and needle 218, greatly facilitates the application of the sutures to the heart annulus, and the application of the prosthetic valve to the heart annulus after the sutures have been so applied, both as will be more particularly described below.

The lower ring 212 is constituted of a plurality of axially-extending ribs 220 circumferentially-spaced around the ring for separating the sutures when pre-loaded onto the handle. Each rib 220 includes an upper section 220a, and a lower section 220b, the two sections being joined by a tapered juncture 220c. The upper sections 220a of ribs 220 are of larger width than the lower sections 220b, so that the upper portion of ring 212, constituted of the upper rib sections 220a, has a larger outer diameter than the lower portion of the ring constituted of the lower rib sections 220b.

Each rib 220 in ring 212 is formed with an axially-extending slit 222 starting from its lower edge and extending to about a mid-portion of the upper rib section 220a. Slits 222 (FIGS. 11, 11a) are adapted to receive the needles 218 (FIGS. 12 and 13) at the free end of each of the sutures 210 when pre-loaded unto the handle 204. The lower edge of each rib 220 is recessed on one side of its respective slit 222 as compared to the other side, as shown at 223 (FIGS. 11, 11a), in order to better facilitate grasping each needle 218 when it is to be removed from its respective slit 222 at the time of the surgical operation.

The upper portions of each rib 220 in the lower ring 212 are formed with longitudinally-extending extensions 220d (FIG. 11) spaced from the outer face of handle 202. The inner faces of these extensions 220d are tapered inwardly from their outer to their inner ends, and their inner ends are formed with slits 224 (FIGS. 11a) at the junctions with handle 202.

The foregoing structure of the lower ring 220 provides a number of advantages which are important both at the time of pre-loading the implement with the sutures 210 and the prosthetic valve 208 before the surgical operation, and also during the surgical operation when the valve and sutures are removed from the implement for insertion into the heart annulus, as will be described more particularly below.

The upper ring 214 secured to the upper end of handle 204 is also formed with a plurality of axially-extending circumferentially-spaced ribs 230, which ribs are also used for separating the sutures 210 when pre-loaded onto the handle. Ribs 230 are of decreasing width from the top to the bottom of ring 214, so that the outer diameter of the ring, as defined by the outer faces of its ribs 230, is of a frusto-conical configuration, being tapered with a decreasing diameter from the top to the bottom of the ring. The recesses or grooves 232 defined by the spaces between the ribs 230 are therefore also of tapered depth, being of largest depth at the top and decreasing in depth towards the bottom of the ring.

Ribs 230 in the upper ring 214 serve as projections for engaging mid-portions of the sutures 210. These projections, together with the projections defined by ribs 220 of the lower ring 212, permit the sutures 210 to be pre-loaded in the above-described longitudinally-folded, circumferentially-spaced condition on handle 204 before the surgical operation is started. The upper edges of projections 230 in the upper ring 214 are preferably slightly tapered outwardly from their inner to their outer edges, in order to more stably hold the sutures in their folded condition.

Upper ring 214 is provided with a plurality of colored dots 240 (FIG. 11), in grooves 232 equally spaced around the circumference of the ring. Preferably, ring 214 includes three such colored dots, spaced 120° from each other. Corresponding colored dots 242 are provided in the grooves between ribs 220 in the lower ring 212. The purpose of these colored dots 240 and 242 is to aid in guiding the surgeon, when removing the sutures 210 during a surgical operation to enable him to more uniformly apply the sutures around the circumference of the heart annulus, thereby decreasing the possibility of heart leakage caused by unequal spacings of the sutures.

The upper end of handle 204 is provided with a cross-bar 244 having inner curved surfaces 246. These surfaces are gripped by the user's fingers during the surgical operation particularly when the implement is used for applying traction, as will be described more particularly below. When the implement is so gripped, the user's thumb presses against knob 248 centrally of the cross-bar 244, thereby enabling the user to firmly grip the implement handle by pressing his thumb against knob 248, and his two adjacent fingers against the curved surfaces 246 of the cross-bar 244.

Knob 248 is fixed to a shank 250 extending through handle 202 for its complete length to the prosthetic valve holder 206 at the opposite end. Shank 250 is threaded at its lower end 252 such that rotating knob 248 causes the shank to advance or retract with respect to a pair of shoulders 252 integrally formed with the two jaws of the prosthetic valve holder 206. Shoulders 252 are normally spaced from each other by a small spacing 254, the shoulders being engageable by the rounded tip of shank 250 for spreading apart the jaws of the valve holder.

The implement illustrated in FIGS. 11 and 12 of the drawings may be used in the manner shown in FIGS. 13-16, as follows:

Before the surgical operation, the implement 202 is first pre-loaded with the prosthetic valve 208 by applying the valve over the two jaws of holder 206 and then rotating knob 248 to advance shank 250 to spread the jaws into firm engagement with the inner face of the valve rim.

All the sutures 210 are then pre-applied to the holder 202, one after the other, each in the following manner:

One end of the suture is fixed to the lower ring 212 by applying its needle 216 across the top edge of its respective rib 220 in the lower ring 212; and the suture is then passed through the space between that rib and the next adjacent one. Needle 218 at the opposite end of the suture is passed through the prosthetic valve 208 on holder 206. The suture is then returned back to the lower ring 212 and passed through the space between its respective rib 220 and the next adjacent one (on the opposite side), over the top of its respective rib 230 in the upper ring 214, back to the lower ring 212 and around the lower edge of its respective rib 220, back to the top of its respective rib 230 in the upper ring 214, and then back to the lower ring 212. Its needle 218 is then inserted within slit 222 of its rib 220 in the lower ring 212. All the other sutures 210, of which there may be 12-20 as mentioned earlier, are applied in the same manner.

The above procedure for pre-loading the implement with the prosthetic valve 208 and the plurality of sutures 210 is performed before the surgical operation, either by the manufacturer supplying the implement so pre-loaded, or by the hospital attendants.

Figure 14:
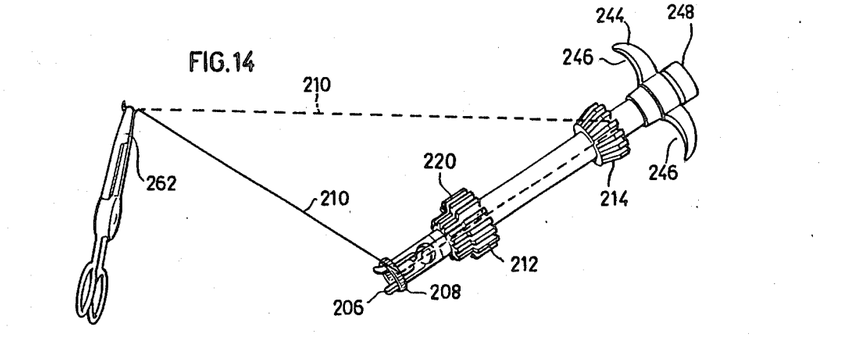
FIG. 14 illustrates how each removed suture in the instrument of FIG. 11 is unfolded for application to the heart annulus.
Figure 15:
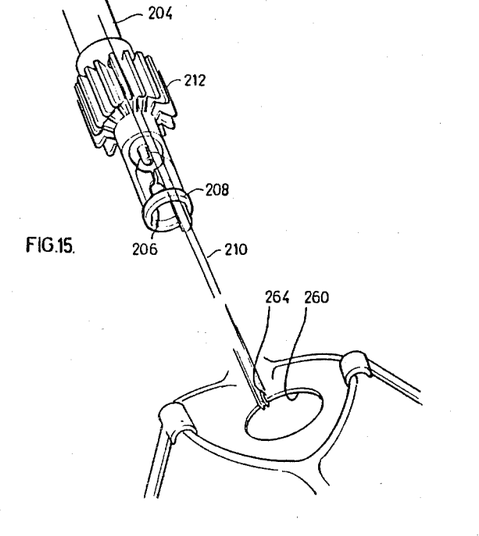
FIG. 15 illustrates the manner of applying the suture to the heart annulus with the instrument of FIG. 11.
Figure 16:
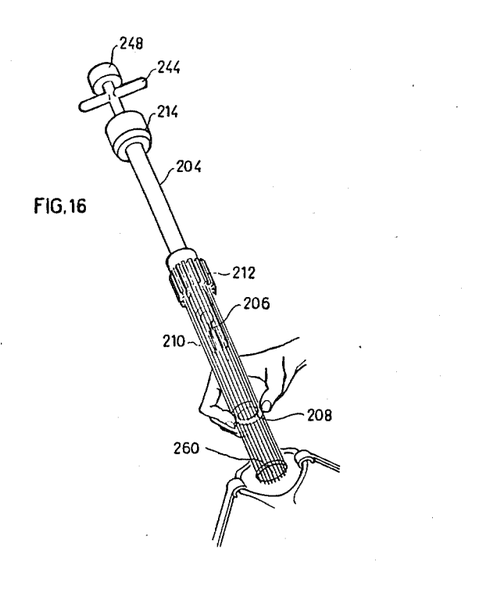
FIG. 16 illustrates the manner of applying the prosthetic valve to the heart annulus with the instrument of FIG. 11 after all the sutures have been applied thereto.

During the surgical operation, the natural, defective valve is first surgically removed from the patient, and the heart annulus 260 (FIGS. 15 and 16) is prepared for receiving the prosthetic valve 208. The pre-loaded implement 202 is held by an attendant over the subject's body with the prosthetic valve 208 facing, but spaced a distance from, the heart annulus 260, as shown in FIG. 15. Each suture is then individually removed from its slit 222 in ring 212, e.g., by gripping its needle 218 with a forceps 262 (FIG. 13), and then unfolding the suture from both rings 212 and 214 (FIG. 14). The suture needle 218 is then passed through the heart annulus 260 (FIG. 15) to form an "over-and-over" stitch 264; again through the valve 208 while the valve is still retained by holder 206 externally of the body, and is then applied over the upper end of its respective rib 220 and wedged into its slit 224.

After the first suture has thus been applied, an attendant holding handle 204, particularly between the finger grips 246 and knob 248, lightly pulls it away from the heart annulus 260 to thereby apply a traction force retracting the annulus and also placing the so-applied suture 210 under tension. All the remaining sutures 210 are applied in the same manner as described above, one after the other, while the attendant maintains the traction force on the implement, thereby maintaining the retraction of the annulus and the tension on each suture after it has been applied in its turn.

After all the sutures, (e.g. 12-20, according to the particular case) have been so applied, and while all the sutures are maintained under tension as described above, knob 248 is rotated in order to withdraw its shank 250 from engagement with shoulders 252 of valve holder 206, whereby the jaws of valve holder 206 move towards each other under their inherent resiliency to release the prosthetic valve 208. The surgeon, while grasping the released valve between his thumb and index finger as shown in FIG. 6, slides the valve along the tensioned sutures 210 towards and into the heart annulus 260. Each suture is then tied in place by first releasing its opposite end from ring 212, and then forming one or more knots to securely hold the valve 208 within the heart annulus 260. After all the sutures have thus been secured, their free ends are trimmed.

It will be appreciated that the suture implement illustrated in FIGS. 11 and 12 provide the same advantages as the previously described ones. Thus, pre-loading the implement before the operation with the prosthetic valve and the sutures very substantially reduces the time required during the surgical operation; in additon, the implement serves as a common retractor for exposing the complete annulus during the operation; further, since the sutures are all maintained under tension, there is substantially less danger of entanglement; moreover, the tensioned sutures act as a guide for guiding the valve into proper position within the heart annulus, e.g. during the steps illustrated in FIGS. 6 and 16, thereby better assuring correct placement of the valve in a minimum of time.

In addition to the foregoing advantages, the improved implement construction illustrated in FIGS. 11 and 12 provides still further advantages. Thus, the provision of the cross-bar 244, particularly the two finger-gripping surfaces 246 and the thumb-gripping knob 248, enables the user to firmly grip the implement for applying tension to the sutures, while substantially reducing the overall size of the implement as compared to that illustrated in FIGS. 1-10. In addition, the construction of the lower ring 220 provides a recessed arrangement protecting the needles 218, thereby permitting the implement to be placed on a table or other horizontal surface without the possibility of dislodging or damaging the needles. Further, the upper, larger-diameter section of the lower ring 212 permits the attendant to conveniently hold the lower part of the handle with one hand while gripping the cross-bars 246 with the other hand, to provide firm control of the implement when applying tension to the sutures.

Figure 13:
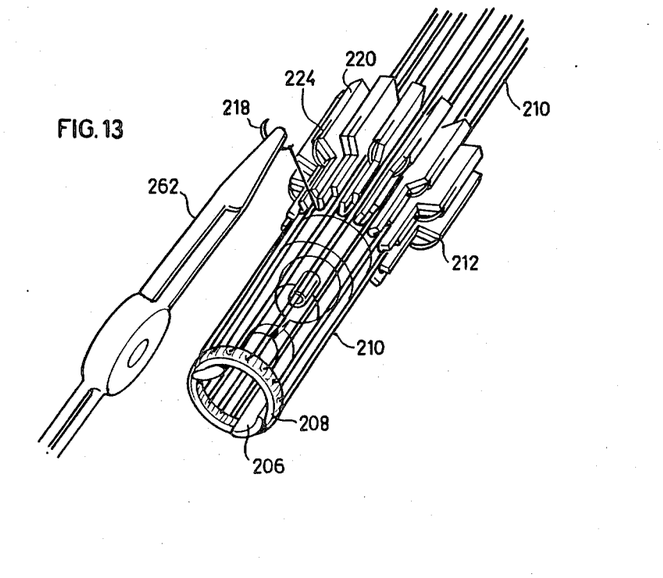
FIG. 13 is a fragmentary view illustrating the lower end of the surgical implement of FIGS. 11 and 12 in its pre-loaded condition, and particularly showing the manner of removing each suture for applying same to the heart annulus.

A still further advantage of the FIGS. 11 and 13 arrangement is that by securing the sutures to the lower ring 212, rather than to the upper ring 214, the surgeon can quickly see by observing the presence or absence of sutures in the space between the two rings, what sutures are yet to be applied and what sutures have been applied. Also, securing the sutures to the lower ring further decreases the possibility of entanglement as compared to an arrangement wherein the sutures are secured to the upper ring.

Still further, the construction of the lower ring 212, enabling each suture after being applied to the heart annulus 260 to be wedged into its slit 224 at any desired point along the length of the suture, better assures that the sutures will all be of substantially equal length, and will therefore apply uniform tension when the implement is used to apply traction. This better facilitates the exposing of the complete annulus during the operation, and also decreases the possibility of entanglement between sutures. Finally, the provision of the colored buttons 240 in the upper ring 214, and the colored buttons 242 in the lower ring 212, provides a clear guidance to the surgeon for assuring an equal distribution of the sutures around the heart annulus, thereby decreasing the possibilty of leakage.

While the invention has been described with respect to several preferred embodiments, it will be appreciated that many other variations, modifications and applications of the invention may be made. For example, it could be used for attaching a patch over a ventricular or septal defect wherein the holder is a known one for holding the patch, and wherein the tensioned sutures guide the patch to proper position over the defect.

What is claimed is:

1. A surgical instrument to aid in suturing a prosthetic valve into a heart annulus, comprising:
    a manually grippable handle;
    a holder carried at one end of the handle for releasably holding a prosthetic valve to be pre-loaded thereon;
    a first ring fixed to the handle and having means for securing thereto one end of a plurality of sutures to be pre-loaded onto the handle with each suture carrying a needle at its opposite end passing through the prosthetic valve when pre-loaded on said handle;
    and a second ring fixed to said handle and including a plurality of circumferencially-spaced projections each engageable with an intermediate portion of a suture for releasably retaining the plurality of sutures each pre-loaded in folded condition on the handle and extending longitudinally thereof;
    said two rings being located on said handle such that each suture has a length between said prosthetic valve and said needle-carrying end of the suture which is at least twice the length of the suture between said secured one end and said prosthetic valve.

2. The surgical instrument according to claim 1, wherein said two rings are located on said handle such that each suture has a length between said prosthetic valve and said needle-carrying end of the suture which is at least three times the length of the suture between said secured one end and said prosthetic valve.

3. A surgical implement according to claim 1, wherein:
    said first ring is secured to said handle adjacent to the end thereof carrying said holder; and
    said second ring is secured to said handle adjacent to the opposite end thereof and includes said projections one for each suture engageable by a mid-portion of the respective suture to permit same to be folded back to said first ring to provide, in the suture pre-loaded condition of the implement, at least two folds of the suture between said first and second rings.

4. The implement according to claim 3, wherein said first ring also includes a projection for each suture engageable by another mid-portion of the respective suture to permit same to be folded back to said second ring to provide, in the suture pre-loaded condition of the implement, at least four folds of the suture between said first and second rings.

5. The implement according to claim 3, wherein said first ring further includes a wedging surface for each suture for receiving a mid-portion of the respective suture after unloaded from the implement and its needle end applied through the heart annulus into which the prosthetic valve is to be sutured, each of said wedging surfaces being configured so as to wedgingly receive its respective suture at any mid-portion thereof to tension the suture when the implement is used for applying traction to the annulus.

6. The implement according to claim 5, wherein said first ring is formed with a plurality of radially extending circumferentially-spaced slits, one for each suture, for removably receiving the needle thereof.

7. The implement according to claim 6, wherein said plurality of radially-extending slits are formed in the lower end of said first ring adjacent to said valve holder, the upper end of said first ring remote from said valve holder being of larger outer diameter than the lower end thereof to protect said needles when the implement is loaded with said sutures and needles, and also to provide a convenient hand-grip for the implement when applying traction to the annulus after the suture has been applied thereto.

8. The implement according to claim 3, wherein said first ring is formed with a plurality of longitudinally-extending circumferentially-spaced ribs for separating said sutures when pre-loaded in folded condition on said handle.

9. The implement according to claim 8, wherein the upper ends of said ribs in said first ring are formed with longitudinally-extending tapered extensions spaced from the outer face of said handle and terminating in wedging surfaces between said ribs and handle, and effective to guide mid-portions of the sutures into their respective wedging surfaces for firmly retaining the sutures therein when applying traction to the heart annulus.

10. The implement according to claim 1, wherein the outer face of said second ring is of frusto-conical configuration, having a larger diameter at its upper end remote from said valve holder.

11. The implement according to claim 1, wherein said handle includes a cross-bar at the upper end thereof for gripping between the user's two fingers and thumb.

12. The implement according to claim 11, wherein said handle includes a knob centrally of the cross-bar for engagement by the user's thumb, which knob is rotatable to actuate said holder to release the prosthetic valve held thereby.

13. A surgical instrument to aid in suturing a prosthetic valve into a heart annulus, comprising:
    a manually grippable handle;
    a holder carried at one end of the handle for releasably holding a prosthetic valve to be pre-loaded thereon;
    a first ring on said handle adjacent to the end thereof carrying said holder and having means for securing thereto one end of a plurality of sutures to be pre-loaded onto the handle with each suture carrying a needle at its opposite end passing through the prosthetic valve when pre-loaded on said handle;
    and a second ring on said handle adjacent to the end opposite to said holder for releasably retaining the plurality of sutures each pre-loaded in folded condition on the handle and extending longitudinally thereof;
    said second ring including a projection for each suture engageable by a mid-portion of the respective suture to permit same to be folded back to said first ring to provide, in the suture pre-loaded condition of the implement, at least two folds of the suture between said first and second rings.

14. The implement according to claim 13, wherein said first ring also includes a projection for each suture engageable by another mid-portion of the respective suture to permit same to be folded back to said second ring to provide, in the suture pre-loaded condition of the implement, at least four folds of the suture between said first and second rings.

15. The implement according to claim 13, wherein said first ring further includes a wedging surface for each suture for receiving a mid-portion of the respective suture after unloaded from the implement and its needle end applied through the heart annulus into which the prosthetic valve is to be sutured, each of said wedging surfaces being configured so as to wedgingly receive its respective suture at any mid-portion thereof to tension the suture when the implement is used for applying traction to the annulus.

16. The implement according to claim 15, wherein said first ring is formed with a plurality of radially extending circumferentially-spaced slits, one for each suture, for removably receiving the needle thereof.

17. The implement according to claim 16, wherein said plurality of radially-extending slits are formed in the lower end of said first ring adjacent to said valve holder, the upper end of said first ring remote from said valve holder being of larger outer diameter than the lower end thereof to protect said needles when the implement is loaded with said sutures and needles, and also to provide a convenient hand-grip for the implement when applying traction to the annulus after the suture has been applied thereto.

18. The implement according to claim 13, wherein the outer face of said second ring is of frusto-conical configuration, having a larger diameter at its upper end remote from said valve holder.

* * * * *